United States Patent [19]

Cottonaro et al.

[11] Patent Number: 4,920,967

[45] Date of Patent: May 1, 1990

[54] DOPPLER TIP WIRE GUIDE

[75] Inventors: Cliff N. Cottonaro; Scott M. Evans; David R. Pflueger; Huntly D. Millar, all of New York, N.Y.

[73] Assignee: Pfizer Hospital Products Group, Inc., New York, N.Y.

[21] Appl. No.: 83,610

[22] Filed: Aug. 11, 1987

Related U.S. Application Data

[63] Continuation-in-part of Ser. No. 888,060, Jul. 18, 1986, abandoned, and a continuation-in-part of Ser. No. 887,291, Jul. 21, 1986, abandoned.

[51] Int. Cl.$^5$ .............................................. A61B 8/00
[52] U.S. Cl. ............................... 128/662.06; 128/772
[58] Field of Search ...................... 128/344, 348.1, 305, 128/772, 660–661, 663, 692, 642

[56] References Cited

U.S. PATENT DOCUMENTS

| | | | |
|---|---|---|---|
| 3,452,742 | 7/1969 | Muller | 128/772 |
| 3,521,620 | 7/1970 | Cook | 128/772 |
| 3,547,103 | 12/1970 | Cook | 128/772 |
| 4,534,363 | 8/1985 | Gold | 128/772 |
| 4,545,390 | 10/1985 | Leary | 128/344 X |
| 4,576,177 | 3/1986 | Webster, Jr. | 128/660.03 |
| 4,587,972 | 5/1986 | Morantte, Jr. | 128/662.06 |
| 4,589,419 | 5/1986 | Laughlin et al. | 128/663 |
| 4,771,788 | 9/1988 | Millar | 128/662.06 X |
| 4,794,931 | 1/1989 | Yock | 128/662.06 X |

FOREIGN PATENT DOCUMENTS

2424733 1/1980 France .................. 128/663

OTHER PUBLICATIONS

Wells, P. N. T., "Biomedical Ultrasonics", Academic Press, N.Y., 1977 (pp. 52–53).
Hisanaga, K. et al., "A New Trans-Digestive Tract Scanner With a Gastro-Fiber-Scope", Proc. 23rd, AIUM, 1978, p. 170.
Boba, K., "UTS Diagnostic Apparatus", Europ. Pat. Appln. Publ. No. 0065275, publ. 24-11-82.

Primary Examiner—Francis Jaworski
Attorney, Agent, or Firm—Peter C. Richardson; Lawrence C. Akers; Robert F. Sheyka

[57] ABSTRACT

An invasive, fluid velocity measuring wire guide particularly adapted and of a size (less than 0.030 inch) for subselective placement in the coronary arterial tree, which includes a Doppler mechanism for determining the blood flow velocity in the region of the distal end of the wire guide. Although the wire guide is particularly adapted for diagnosing coronary arterial disease subselectively; it is of such a size and manipulability to be useful in other blood flow and biological fluid flow analyses. Preferably, the wire guide is flexible and steerable for precise placement. The wire guide includes an elongated wire member having a Doppler crystal attached in longitudinal alignment at its distal end. Electrical leads extend from the Doppler crystal along the wire member to the appropriate test equipment for measuring the fluid flow velocity in the region of the Doppler crystal. Preferred embodiments of the Doppler means include piezoelectric crystals and piezoelectric polymers. Also disclosed is a guide wire with a laser Doppler means.

8 Claims, 5 Drawing Sheets

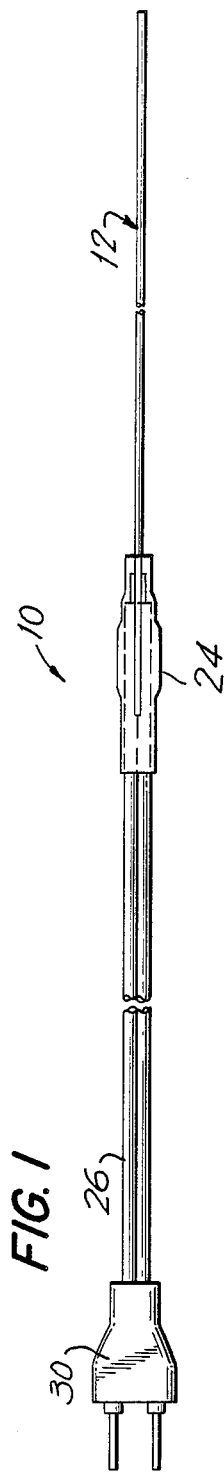
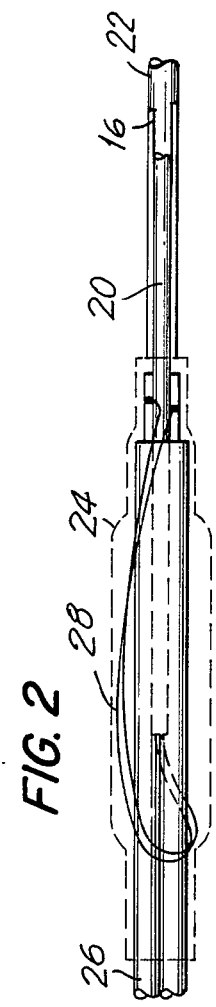
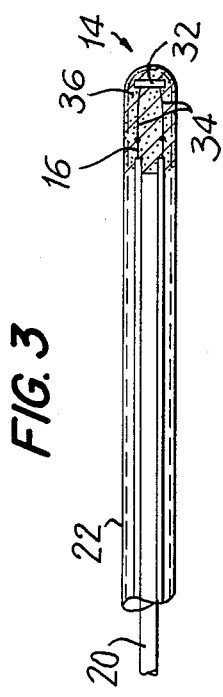
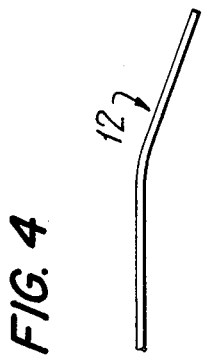
FIG. 1
FIG. 2
FIG. 3
FIG. 4

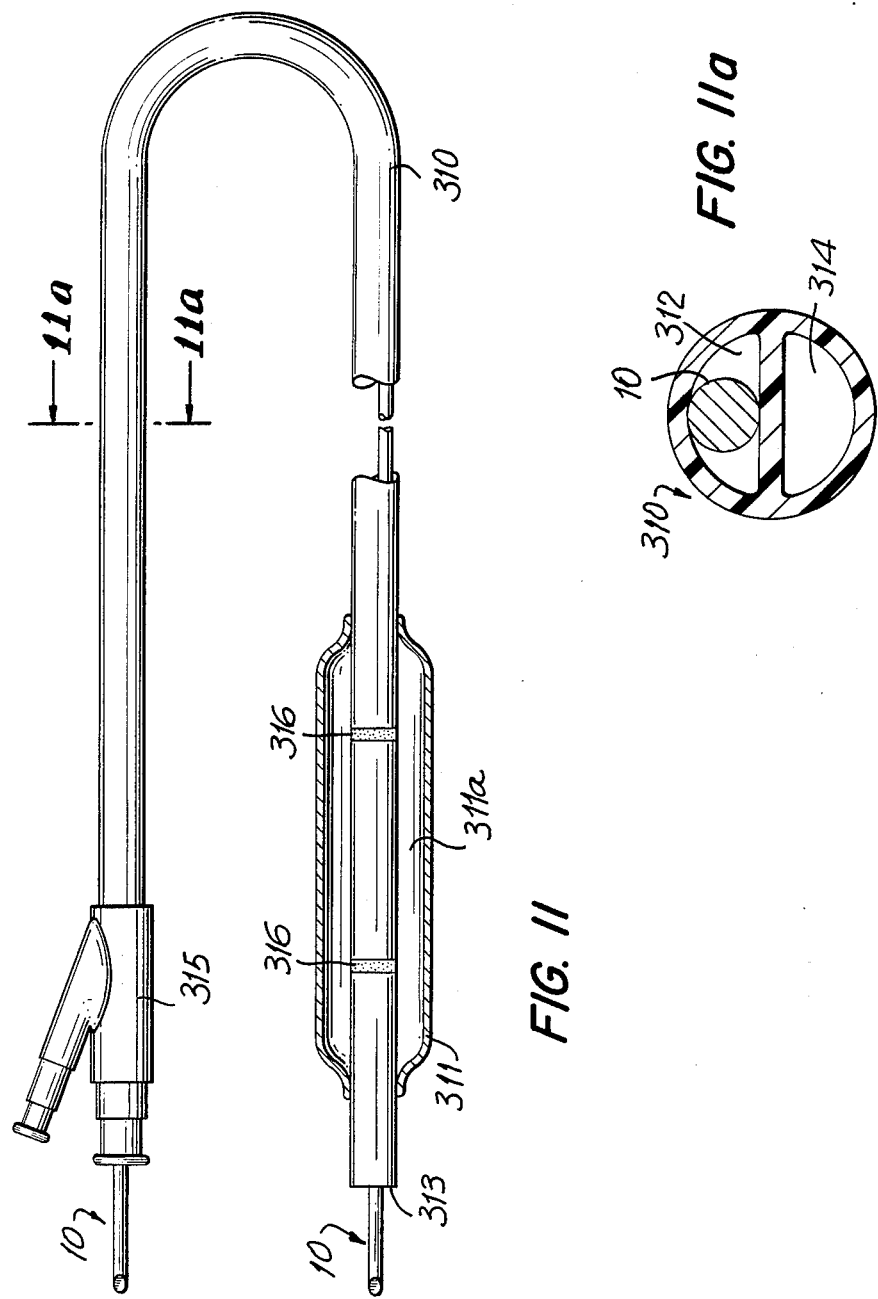

DOPPLER TIP WIRE GUIDE

RELATED APPLICATIONS

This application is a continuation-in-part of U.S. Ser. No. 888,060 filed July 18, 1986, and now abandoned and U.S. Ser, No. 887,291 filed July 21, 1986, and now abandoned.

BACKGROUND OF THE INVENTION

This invention relates to wire guides having a Doppler mechanism for determining in vivo flow velocity of a biological fluid. In particular, it relates to a flexible, steerable, fluid velocity measuring wire guide which is receivable in a catheter and positionable sub-selectively in the coronary arterial tree for diagnosing heart disease.

Coronary artery disease is a common medical problem, particularly in the United States, and often manifests itself as a constriction or stenosis in the arterial tree. Coronary artery disease can lead to increased arterial stenosis and gradual diminution of reactive hyperemic response. Because arterial disease is commonplace, it is important to properly diagnose the presence of specific lesions or vessel stenosis and to properly evaluate the efficacy of treatment of these arterial lesions.

Stenoses past the coronary ostium are not only difficult to identify and treat, but are also prime concern because of their effect on available coronary vasodilator reserve. To identify coronary disease, the arteriogram has long been used to determine the presence and extent of stenoses. Applicant's co-pending application Ser. No. 775,857 (incorporated herein by reference) discusses the inadequacies of the arteriogram as an indication of the presence and nature of coronary arery disease. See, White, et al., *Interpretation of the Arteriogram*, 310 New Eng. J. Med. 819-824, 1984).

Transluminal angioplasty (enlargement of the lumen of a stenotic vessel using an intravascular catheter) was initiated by Dotter and Judkins in the mid-1960's. However, prior to the work of Gruentzig (mid-1970's), coronary stenoses were usually treated by open heart surgery, such as coronary artery bypass surgery. Gruentzig developed an inflatable non-elastomeric balloon mounted on a small catheter which could be introduced into the vessel across the stenoses, and then inflated with a sufficient force to enlarge the stenotic lumen. Since the pioneering work of Gruentzig in the mid-1970's, there have been significant improvements in the equipment and techniques developed for his percutaneous transluminal coronary angioplasty (PTCA) procedure. In the United States, the growth in the number of PTCA procedures being performed has been dramatic—approximately 1,000 PTCA procedures were performed in 1980 and over 100,000 procedures were performed in 1986. PTCA procedures represent a major alternative to bypass surgery and have enjoyed an increasing success rate.

Although PTCA procedures have become increasingly successful, a major cause of failures is the inability to accurately identify the regions of stenoses and to evaluate the success of the angioplasty across the stenotic vessel. That is, the arteriogram is still the prime method of identifying and evaluating the stenosis and can lead to any number of mistakes in interpretations —such as observer error, superselective injection, pulsatile injection of contrast media, total occlusion, etc. Further, angiographic evaluation of the region of stenoses after the PTCA procedure is often difficult, owing to the poor definition of the vessel after angioplasty. Thus, while such coronary angioplasty techniques have been relatively successful in treating the regions of stenosis, the unreliability of the arteriogram has been a significant detraction from the efficiency of angioplasty.

Because a PTCA procedure uses a steerable guidewire to place the angioplasty balloon catheter sub-selectively in the coronary vessels, it would be a significant advance in the art and a major improvement over the arteriogram if a guidewire were devised which was capable of getting a direct indication of blood flow in a particular region of the coronary vessel. Further, it would be a significant advance if such a guidewire capable of measuring fluid velocity were devised which was useful in measuring velocity of other biological fluids and was easily positioned in a biological vessel of interest.

The velocity determining wire guide of the present invention provides one solution for subselectively identifying the nature and extent of coronary artery disease, and further provides a device which is useful in invasively determining biological fluid flow in any small or constricted vessel. Advantageously, the wire guide of the present invention is of such a size (less than 0.030 inch) that it will easily fit down the central lumen or side channel of an angioplasty catheter which itself is such a size to be subselective in the coronary arterial tree. Preferably, the wire guide hereof is steerable and is useful not only as a probe for locating regions of heart disease, but also as a guide for an angioplasty catheter.

SUMMARY OF THE INVENTION

Broadly speaking, the wire guide of the present invention includes an elongated member which is generally longitudinally inelastic and flexible for threading engagement with the catheter. A Doppler mechanism is coupled to the distal end of the elongated member and is operable for determining the velocity of the blood when inserted in the arterial tree. Electrical lead means coupled to the Doppler mechanism run along the member towards the proximal end of the guide wire, such that blood velocity can be determined as the wire guide is selectively advanced in the arterial tree.

In a preferred form, the wire guide includes an elongated support wire having a pair of electrical leads running along the length thereof, with the leads and support wire encapsulated in an insulator sheath. A Doppler crystal is connected to the leads and is secured to the distal end of the sheath with the face of the Doppler crystal generally perpendicular to the longitudinal axis of the sheath. In an alternative embodiment, the distal end of the wire guide is bent at a small angle, such that torque control of the support wire reorients the distal end carrying the Doppler crystal for selective steerability and better Doppler signal reception.

In another preferred embodiment, the elongated member comprises a helically wound spring coil defining a central passageway therein. The Doppler crystal is fitted to the distal end of the spring coil and electrical leads are coupled to the Doppler crystal and received within the central passageway. An elongated inelastic fixed core wire is secured to the distal end and proximal end of the spring coil to prevent longitudinal elongation of the spring coil. In a alternative embodiment, the distal portion of the spring coil is in a "J" shaped configuration. Advantageously, a movable coil wire is shiftably received in the central passageway and operable such that when it is shifted into the region of the "J" shaped configuration, the region tends to straighten out. Thus, the movable core allows the doppler crystal to be oriented as desired and allows the distal end of the spring coil to be directionally aligned for subselective movement in the arterial tree.

In another embodiment, the elongated member forms a sheathing means around a laser doppler means.

BRIEF DESCRIPTION OF THE DRAWINGS

FIG. 1 illustrates a fragmentary, side elevational view of a velocity measuring wire guide in accordance with the present invention;

FIG. 2 is an enlarged, fragmentary, sectional view of a proximal portion of the wire guide illustrated in FIG. 1;

FIG. 3 is an enlarged, fragmentary, sectional view of the distal region of the wire guide of FIG. 1;

FIG. 4 is a fragmentary, side elevational view of an alternative embodiment of the distal region of the wire guide of FIG. 1;

FIG. 11 depicts a dilatation catheter in combination with the guide wire of the present invention.

FIG. 11a is a cross sectional view taken along line 11a—11a of FIG. 11 and depicts the guide wire of the present invention in place in the dilatation catheter.

DETAILED DESCRIPTION OF THE INVENTION

Figure 5:
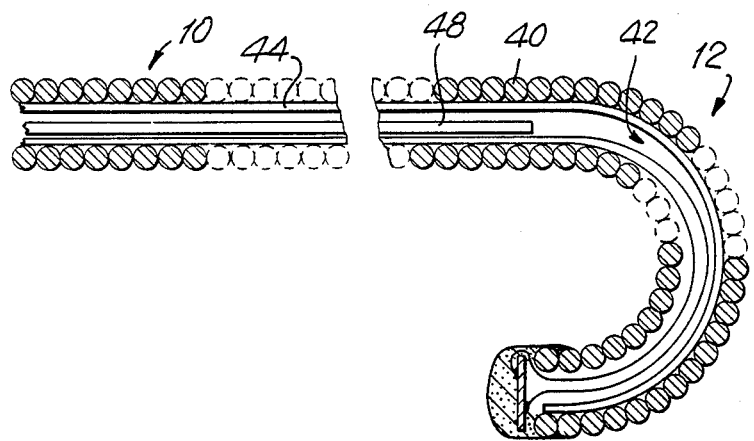
FIG. 5 is an enlarged, fragmentary, sectional view of a wire guide in accordance with the present invention which includes a coil spring in a "J" shaped configuration and a movable core.

Turning now to the drawings, a wire guide 10 in accordance with the present invention is illustrated in various embodiments. Broadly speaking, the wire guide 10 includes an elongated, flexible, longitudinally inelastic wire member 12, Doppler mechanism 14 and electrical leads 16 running the length of the member 12.

In more detail, in the embodiments depicted in FIGS. 1-4 the wire member 12 includes an elongated support wire 20 which is flexible and longitudinally inelastic, and torquable in the sense that a twisting moment at the proximal end will impart a twisting moment at the distal end. The support wire 20 is preferably a stainless steel piano wire and in the preferred embodiment, has an approximate outer diameter of 0.012 inches. The electrical lead 16 comprises a pair of electrical connector wires juxtaposed in adjoining relationship to the support wire 20. The leads 16 have an approximate outer diameter of 0.002 inches and preferably include a copper conductor having four layers of a thin nylon insulation. A cylindrical, insulator sheath 22 of plastic, nylon, polyurethane, or other suitable insulating material envelopes the support wire 20 and electrical leads 16, to present an outer diameter preferably less than 0.030 inches, and in the preferred embodiment having an outer diameter of 0.019 inches.

Turning to FIG. 2, the sheath 22 is received in an insulating sleeve 24 substantially as shown. Doppler connector cable 26 leads into the opposite end of the sleeve 24 and is connected to the lead 16 by the coupling wires 28 as shown. As illustrated in FIG. 1, the connector cable 26 terminates in a universal coupling 30.

As shown in detail in FIG. 3, the Doppler mechanism 14 includes a generally flat Doppler crystal 32 which is preferably a piezoelectric ceramic crystal comprising a lead-zirconate-titanate material. The Doppler crystal 32 is approximately 0.003 inch in thickness and is designed to resonate at 20 megahertz. A pair of conductors (preferably gold) are attached to the crystal 32 such that the Doppler crystal 32 operates as a pulsed Doppler, operating alternatively as a transmitter and receiver. The conductors 34 are connected by the electromechanical joints to the leads 16. A potting compound 36, such as an epoxy resin, secures the Doppler crystal 32 in the circular opening defined by the sheath 22. As can be seen in FIG. 3, the distal end of the support wire 20 terminates prior to the distal end of the sheath 22, leaving a void which is filled by the potting compound 36.

In another preferred embodiment, the piezoelectric transducer 32 is a piezoelectric material which is an electret of high polymeric material or which is an electret of a composite consisting of a high polymeric resin and a piezoelectric ceramic, each of the above being defined as a piezoelectric polymeric material.

Piezoelectric polymeric materials can be used in the form of electrets obtained by a manufacturing method which comprises stretching films or extrusions of thermoplastics such as polyvinyl fluoride, polyvinylidene fluoride, polyvinyl chloride, polyacrylonitrile, polycarbonate etc., to several times their original length while at a temperature near the softening temperature, forming electrodes on both surfaces of the resulting stretched film or extruded material either by vapor deposition of silver, gold, or aluminum or by chemical plating, with the heating from room temperature to the temperature near the softening point being accomplished under a condition of applied electric field of from about 100 to about 700 KV/cm DC, and then cooling the product.

Alternatively, as a piezoelectric polymeric material, suitable electrets can be obtained by manufacturing a composite which comprises mixing from 90 to 10% by volume of piezoelectric ceramics with from 10 to 90% by volume thermoplastic resin. The thermoplastic resin is a crystalline and polar resin such as polyacetal, vinylidene fluoride resin, or polyamide. Alternatively, the electrets can be obtained by manufacturing a composite which comprises mixing from 90 to 10% by volume piezoelectric ceramics with from 10 to 90% by volume of a blend polymer. The blend polymer is obtained by blending 99 to 20% by weight of the thermoplastic resin and 1 to 80% by weight of a polar polymer such as chloroprene rubber, acrylonitrile butadiene rubber, epichlorohydrin rubber, chlorinated polyethylene and urethane rubber. The resulting composite is then molded into a film of 5–500 um thickness. The molded composite is heated from about 400° C. to about 1000° C. after forming metal layers on its opposite sides by vapor depositing or plating silver or aluminum, and applying thereto an electric field of direct current above 50 amps. Thereafter, the molded composite is cooled.

If the piezoelectric ceramic employed is a lead-zirconium-titanate ceramic, a typical manufacturing process comprises adding from 10 to 90% by volume of the thermoplastic resin to a lead-zirconium-titanate ceramic solution of about 0.2 to 45 um diameter, molding the resulting composite, forming the electrodes on the surface and electretizing the resulting molded composite. The piezoelectric polymeric material is cut to an appropriate size and adhered to the guide wire. The mounting of the piezoelectric polymeric material is as illustrated in FIG. 1 with the electrically insulating material 36 encapsulating the piezoelectric polymeric material and electrical leads 16. Although FIG. 1 depicts the piezoelectric transducer radially oriented in relation to the elongated body 20 of the guide wire 10, such an orientation is not absolutely necessary and the piezoelectric material can be axially oriented in relation to the elongated body 20. The piezoelectric transducer can also be constructed so that the transmission of ultrasonic energy is either in a longitudinal or radial direction relative to the longitudinal axis of the guide wire.

As can be appreciated by those skilled in the art, Doppler mechanism 14 is connected through the universal coupling 30 to operate as an ultrasonic pulsed Doppler device capable of measuring the velocity of a fluid. See e.g., C. Hartley and J. Cole, *Pulsed Doppler Flow Measurement*, 37 J. App. Phys., 626–629 (1974) (incorporated herein by reference).

Comparing FIGS. 1 and 4, it is seen that FIG. 4 presents a slightly different embodiment in which the distal region of the wire guide 10 (FIG. 4) is bent at a slight angle relative to the remaining longitudinal alignment of the member 12. Thus, the embodiment of FIGS. 1–3 presents a "straight" wire guide while the FIG. 4 embodiment has a "hockey stick" orientation of its distal region. In some applications, the FIG. 4 embodiment allows better steerability (torquing the member 12) to orient the distal end towards the coronary vessel of interest.

Figure 6:
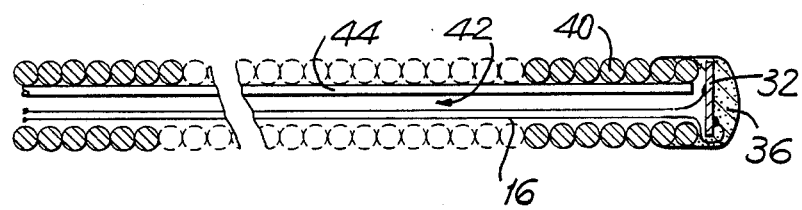
FIG. 6 is an enlarged, fragmentary, sectional view of a wire guide which includes a straight coil spring.
Figure 7:
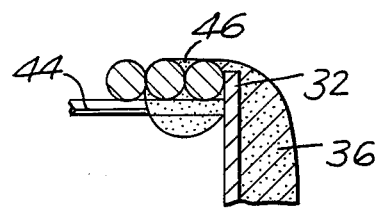
FIG. 7 is an enlarged, fragmentary, sectional view showing in detail the joinder of the Doppler crystal to the coil spring.

Turning now to FIGS. 5–8, further embodiments of the distal region of the wire guide 10 in accordance with the present invention are illustrated. In the FIGS. 5–8 embodiments, the member 12 comprises a helically wound spring coil 40 having an annular cross section to define a central passageway 42. The outer diameter of the spring coil 40 is preferably less than 0.030 inches and as illustrated, is less than 0.019 inch, such that the wire guide 10 will easily fit in the lumen or coupling channel of a dilation catheter or the like. An elongated fixed core wire 44 is coupled to the spring coil 40 at the distal and proximal ends to prevent longitudinal elongation of the spring coil 40 during manipulation. FIG. 7 shows the weld 46 securing the fixed core 44 to the last two winds of the spring coil 40 at the distal end of the wire guide 10, it being understood that the fixed core 44 is similarly secured to the proximal end.

Figure 8:
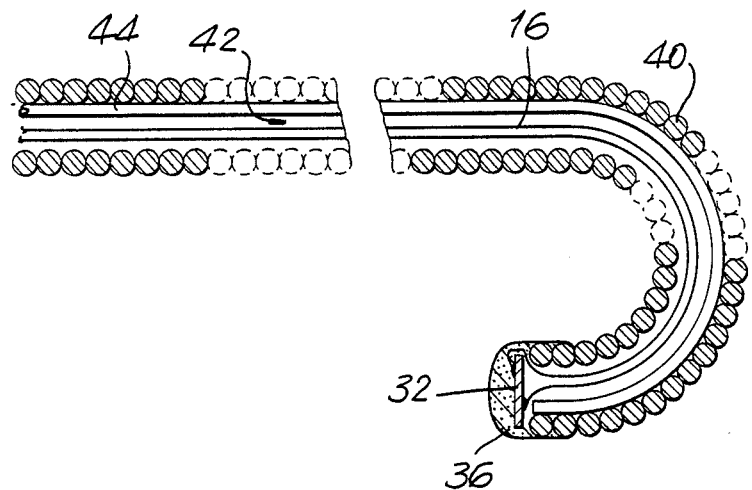
FIG. 8 is an enlarged, fragmentary, sectional view of a wire guide in accordance with the present invention having a "J" shaped distal region without a moveable core.

In the embodiments of FIGS. 5 and 8, the distal region of the wire guide 10 is made to assume a "J" shaped configuration in its normal static state. While an introducer (not shown) is commonly used to straighten the "J" shaped configuration during percutaneous insertion, the embodiment of FIG. 5 additionally includes an elongated movable core 48 shiftably received in the central passageway 42. As those skilled in the art will appreciate, the movable core 48 is usually not flexible enough to conform to the "J" shaped configuration of the central passageway 42. Rather, the movable core 48 as it is advanced to the distal end of the member 12, tends to straighten the distal region towards a more rectilinear orientation. The degree of advancement of the movable core 48 towards the distal end determines the degree of movement of the distal region for a "J" shaped configuration towards a rectilinear orientation. Typically, the movable core 48 is somewhat flexible, such that even with the movable core 48 fully inserted in the central passageway 42, the distal end still presents some angularity (see e.g. FIG. 4).

The Doppler mechanism 14 includes the Doppler crystal 32 secured in place by a potting compound 36 to the distal end of the spring coil 40. In the embodiments of FIGS. 5–8 the potting compound 36 not only secures the crystal 32 to the spring coil 40, but additonally occupies a portion of the central passageway 42 to effect a seal. It should be appreciated, however, that a Doppler crystal 32 can be donut-shaped and the potting compound 36 partially selectively removed to place the central passageway 42 in communication with the blood stream or other biological fluid. Such an alteration would allow the introduction of chemicals or fluids into the blood stream, for example angiogram dye, through the wire guide 10.

The electrical leads 16 are connected to the Doppler crystal 32 in similar fashion as the connections made in the embodiment of FIGS. 1–4. In the embodiments of FIGS. 5–8, the leads 16 are disposed in the central passageway 42 and coupled to a connector cable or similar device leading to an ultrasonic Doppler flow monitor.

The embodiments of FIGS. 5, 6, and 8 differ in only minor detail. FIG. 7 shows a cross-sectional view of the distal end of the member 12 common to the FIG. 5, 6 and 8 embodiments. As should be readily apparent from the drawings, FIG. 6 shows an embodiment in which the distal region of the wire guide is "straight," while FIGS. 5 and 8 show embodiments in which the distal region is in the "J" shaped configuration. In FIG. 5 a movable core 48 is included, while in FIG. 8 only a fixed core 44 is contemplated.

Figure 9:
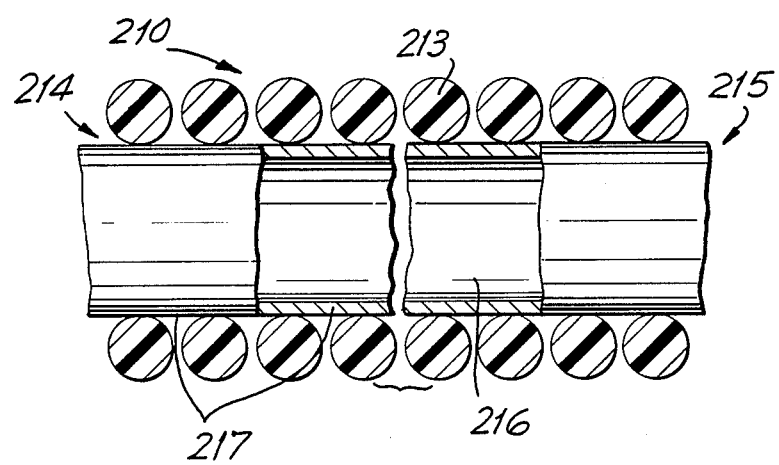
FIG. 9 depicts an alternative embodiment of the guide wire of the present invention wherein the Doppler means is a laser Doppler means.

FIG. 9 depicts another embodiment of the guide wire of the present invention. From FIG. 9, it can be seen that guide wire 210 comprises an elongated body 212 consisting of an insulated helically coiled element 213 having a proximal portion 214 and a distal portion 215 with proximal portion 214 and distal portion 215 configured so as to form a sheathing means. Within elongated body 212 and surrounded by helically coiled element 213 is optical fiber 216 supported within helically coiled element 213 by an outer sleeve 217. Suitable materials of which outer sleeve 217 may be comprised include flexible plastics and other flexible polymers.

Figure 10:
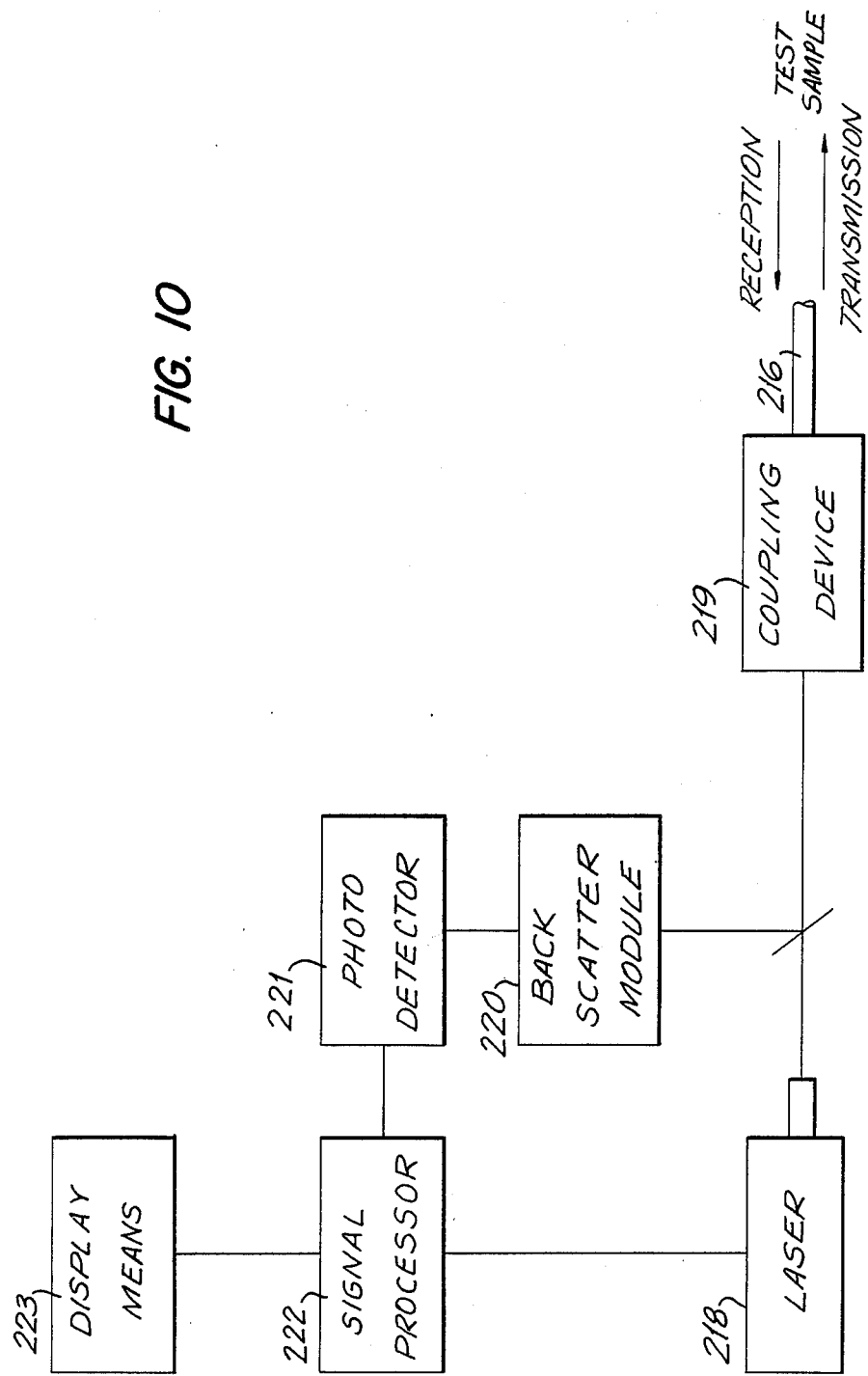
FIG. 10 depicts the circuitry controlling the laser Doppler means of FIG. 9.

FIG. 10 depicts a Laser Doppler mechanism of the guide wire of FIG. 9. From FIG. 10, it can be seen that laser 218 transmits light through coupling device 219 from which the light is transmitted through fiber 216 to the test sample. In the practice of the present invention, it is preferred that the Laser Doppler means be operated in the backscatter mode wherein the transmitted signal reflects off objects in the test sample, for example blood cells, or air emboli. In this case, the reflected signal goes to optical fiber 216 which then sends the signal back to backscatter module 220. The received signal from backscatter module 220 is then sent to photodetector 221, to signal processor 222 for comparison to the transmitted signal and finally to display means 223.

Laser source 218 can be any laser source capable of generating light at a wavelength of from about 1 Kilohertz to about 100 Megahertz. Examples of such lasers include helium-neon lasers. Coupling means 219 may be a conventional mechanism for coupling a laser beam to an optical fiber. Such mechanisms include lenses, prisms, collimators etc. Back scattering module 220 is comprised of the necessary optics for isolating the reflected signal. Photodectector 221, signal processor 222 and display means 223 can all be conventional devices and will vary depending on the measurement desired, the laser source, etc.

FIG. 11 depicts a guide wire of the present invention in combination with a balloon dilatation catheter 310. Balloon dilatation catheter 310, particularly when it is intended for use in a coronary artery, is relatively slender and has a substantially circular cross section with, for example, an outer diameter of the order of 0.056 inches. The inner radius of its lumens, of course, are even smaller and its main lumen may be of the order of 0.013 inches radius. The dilation catheter 310 has a dilation balloon 311 at its distal end and a main lumen 312 (see FIG. 5a) which is used typically to deliver liquids such as radiopaque dye or anticoagulants and also may be used to make pressure measurements. The main lumen 312 opens at an outlet 313 at the distal tip. As shown in further detail in FIG. 11a, the dilatation catheter is provided with an inflation lumen 314 which is smaller than lumen 312 and communicates with the interior 311a of the balloon 311 to inflate and deflate the balloon. The proximal end of the catheter may be provided with a Y-fitting 315 to provide communication at the proximal end of the catheter to each of the main lumen 312 and the inflation lumen 314. Balloon 311 may also be provided with radiopaque rings 316 to facilitate fluoroscopic monitoring of its progress and position.

In all embodiments of the guide wire of the present invention, the guide wire has a diameter ranging from 0.010 to 0.065 inches with a preferred diameter of 0.014 inches. Thus, the guide wire fits within the main lumen 312 of the dilatation catheter 310.

In practice, the dilatation catheter 310 is prepared with the guide wire in place extending through main lumen 312 with the distal end of the guide wire incorporating the Doppler means projecting about 2 centimeters distally of the outlet 313 of the dilatation catheter. The guide wire/dilatation catheter assembly is then pushed through an initially placed guide catheter into the coronary artery with the guide wire being used to steer the catheter towards the area of stenosis. When the position of the guide wire/ dilatation catheter has been verified by, for example, the injection of an angiodye, the guide catheter is withdrawn and blood velocity measurements are taken. Since the guide wire of the present invention incorporates a laser or ultrasound Doppler means, when the device is in place in the blood vessel, each acoustic or light burst is transmitted through the blood and reflected by various structures, for example blood cells, vessel wall, plaque etc. The reflected signals are compared to a master oscillatory signal if the Doppler means uses ultrasonic transducer means or a master oscillatory signal if a laser Doppler means is used. The difference between the master signal and the reflected signal is the Doppler shift, which is determined by the well known Doppler equation.

While the wire guide 10 in accordance with the present invention will undoubtedly find utility in a wide variety of medical applications as a diagnostic tool, it is anticipated that wire guide 10 may be particularly advantageously used in PTCA procedures. In a typical PTCA procedure, either a femoral or brachial approach is taken, using a standard percutaneous procedure such as the Seldinger approach. In most angioplasty procedures, a right heart catheter is inserted to monitor baseline filling pressures and ventricular pacing. Such right heart diagnostic catheterization is relatively easy using a balloon-tip, flow directed catheter (e.g. Swan-Ganz catheter, Edwards Laboratory, Santa Ana, Calif.), in view of the less stringent dimensional restrictions of the pulmonary artery.

Manipulating the catheters and guidewire subselectively past the ostium to perform the angioplasty is often a difficult procedure. In most PTCA procedures, a guiding catheter, balloon dilation catheter, and a steerable guide wire are used. The guiding catheter is usually positioned in the ostium of the coronary artery with the dilation catheter positioned within the guiding catheter for advancement over the guidewire. Most dilating catheters have a central lumen for the sliding reception of the guidewire, while some catheters may have an elongated open side channel for engaging the guidewire. The guidewire is specially designed to combine tip softness, radiographic visibility, and precise torque control so that it can be positioned throughout the sometimes tortuous arterial tree and stenotic regions. Because the dilating catheter typically has a small lumen or channel, the guidewires normally have a diameter less than 0.020 inches.

In the common PTCA procedure, baseline angiograms are used for identifying the regions of stenoses and for positioning the guiding catheter and dilating catheter. The dilating catheter and the guidewire are successively advanced through the target stenoses and positioned relative to the lesions for evaluating by a series of contrast injections through either the guiding catheter or dilation catheter. Thus, the guidewire serves as a track which permits safe advancement of the dilation catheter through the region of the stenoses. Once the dilating catheter is positioned, it is successively inflated (sometimes with varying pressures) until the operator believes that the stenosis has been reduced. As previously indicated, after dilation, the stenosis is typically angiographically evaluated and this evaluation has proven to be somewhat deficient.

Turning to use of the wire guide 10 in accordance with the present invention, the embodiments of FIGS. 4, 5 and 8, represent wire guide configurations which offer the best steerability. However, all of the embodiments illustrated in the drawings are positionable by torque, and hence steerable. In the preferred procedure, a steerable wire guide 10 is inserted into the vessel and the dilating catheter inserted into the vessel in operable engagement with the wire guide 10. The wire guide 10 is manipulated past the ostium subselectively into the coronary artery of interest. Typically, an injection of contrast media would be made through the dilating catheter or guiding catheter to verify the position of wire guide 10.

The dilating catheter is shifted sequentially to follow the wire guide 10 into the target stenotic region. Particularly in the embodiment of FIG. 5, the movable core 48 is positioned in the central passageway 42 to orient the distal end of the wire guide 10 to a desired angularity. The member 12 is then torqued to twist the distal end of the wire guide 10 towards the target artery and the wire guide 10 is then advanced into the artery.

It is readily appreciated that while the wire guide 10 is being advanced, the Doppler crystal 32 is taking continuous readings giving the operator an indication of the blood flow velocity in the region of the distal end of the wire guide 10. Advantageously, this constant indication of blood velocity—and hence blood flow—not only aids in positioning the wire guide 10, but also is of great value in determining the efficacy of the PTCA procedure by giving an immediacy of measurement. That is, after the dilating catheter is positioned across the region of the target stenosis and inflated, the operator has a constant indication of a blood flow across the stenosis before angioplasty and after each successive inflation. Thus, the wire guide 10 in accordance with the present invention represents a substantial advance in the art as a tool for identifying and evaluating coronary disease, particularly in evaluating the efficacy of a PTCA procedure.

As an alternative to the preferred method, the wire guide 10 in accordance with the present invention (particularly the embodiments of FIGS. 1 and 6) is useful in conjunction with conventional wire guides currently used in angioplasty. In the alternative method, a conventional wire guide is positioned using standard angiogram techniques and the dilating balloon catheter advanced into the target stenotic region. The conventional wire guide is then removed and the wire guide 10 in accordance with the present invention inserted though the central lumen (or along the side channel) of the balloon catheter. Thus, the wire guide 10 is used primarily as a tool for evaluating the efficacy of the angioplasty, and is not used in the positioning process.

Those skilled in the art will also appreciate that the wire guide in accordance with the present invention has many other in vivo uses outside of the PTCA procedure. It is readily apparent that because of its small size, flexibility, and steerability, the wire guide 10 can function effectively as a diagnostic probe in evaluating blood flow or other biological fluid flow throughout the body.

We claim:

1. A blood velocity measuring wire guide adapted for operative coupling to a catheter, the wire guide comprising:

an elongated flexible support wire having distal and proximal ends which is generally longitudinally inelastic and flexible for threading engagement with the catheter;

Doppler means consisting of a piezoelectric polymeric material mounted to the distal end of said wire for determining the velocity of the blood with the wire guide inserted in a blood vessel, said piezoelectric polymeric material oriented such that the ultrasonic signals are transmitted in a radial direction in relation to said elongated flexible support wire; and electrical lead means operatively mounted to the distal end of said Doppler means and coupled to said wire along its length.

2. A blood velocity measuring wire guide adapted for operative coupling to a catheter comprising:

(a) an elongated insulated, helically coiled wire having a proximal portion and a distal portion forming a sheathing means, (b) Doppler means for transmitting a signal and for receiving a reflected signal said Doppler means comprising at least one light transmitting fiber capable of transmitting a signal and for receiving a reflected signal, said light transmitting fiber being encased by said sheathing means, said Doppler means being capable of determining the velocity of the blood with the wire guide inserted in a blood vessel by transmitting a signal and receiving a reflected signal.

3. The guide wire of claim 2 wherein said guide wire has a diameter ranging from about 0.010 to about 0.065 inches.

4. The guide wire of claim 3 wherein said guide wire has a diameter of about 0.014 inches.

5. The guide wire of claim 2 wherein said light transmitting fiber is adapted to transmit light from a laser source.

6. The guide wire of claim 5 wherein said laser source transmits light at a wavelength of from about 1 Kilohertz to about 100 Megahertz.

7. The guide wire of claim 5 wherein said laser source is a helium-neon laser.

8. The guide wire of claim 5 wherein said laser source is operated in the backscatter mode.

* * * * *